United States Patent [19]

Williams

[11] Patent Number: Plant 5,909

[45] Date of Patent: Mar. 24, 1987

[54] MINIATURE ROSE PLANT NAMED MINUCO

[76] Inventor: Ernest D. Williams, 1510 Lebanon Ave., Dallas, Tex. 75208

[21] Appl. No.: 728,665

[22] Filed: Apr. 29, 1985

[51] Int. Cl.[4] ..... A01H 5/00

[52] U.S. Cl. ..... Plt./6

[58] Field of Search ..... Plt./6, 10

*Primary Examiner*—R. E. Bagwill

[57] ABSTRACT

The subject of the present disclosure is a new and distinct variety of miniature rose plant characterized by the red color of the very double flowers and by the prostrate spreading habit of growth.

1 Drawing Figure

The present invention relates to a new and distinct variety of hardy, low growing ground cover type rose plant of the miniature class; the variety being primarily characterized—as to novelty—by (A) the medium red coloration of the flowers which in general color effect are similar to Red Cascade (miniature—U.S. Plant Pat. No. 3,962) and (B) by the spreading ground cover growth habit.

The variety is further characterized by:

An abundance of bloom, with flowers usually borne in clusters or sprays.

Little or no fragrance.

A plant which is vigorous, of dense, spreading habit with semi-glossy small foliage, with pointed leaflets; the buds and flowers being similar in form and size to Red Cascade (miniature—U.S. Plant Pat. No. 3,962).

The plant, which has a normal height of 8–12 inches and a spread of up to 5 feet, can easily be maintained at lesser spread by occasional trimming.

A plant which grows and blooms satisfactorily outdoors; is good for growing in pots, tubs, hanging baskets or as a ground cover; and provides excellent garden decoration.

The present variety of miniature rose was originated by me at my nursery located at Dallas, Tex., under conditions of careful control and observation, as a seedling of Red Cascade (miniature—U.S. Plant Pat. No. 3,962), the seed parent being Red Cascade with the pollen parent being (supposedly) the same.

Subsequent to origination of the variety I successfully reproduced it, at my nursery as aforesaid, by cuttings; the reproductions having run true in all respects.

The color photograph illustrates the variety, including the foliage, bud and flowers.

Referring now specifically to the new and distinct variety of miniature rose plant, the following is a detailed description thereof in outline; all major color plate identifications being by reference to the British Color Council Horticultural Color Chart, except where common terms of color definition are employed.

Type: Hardy; dense; spreading; seedling; outdoors; garden decoration; potted plant; ground cover.

Class: Miniature. International identification: Minuco. Commercial synonym: Royal Carpet.

Flowers borne: Usually in cluster or spray of 5 to 15 flowers.

Quantity of bloom: Abundant.

Bud:

*Peduncle.*—Medium to long length; slender but sturdy; medium green, sometimes tinted bronze (outdoors); hairs — several and small.

*Before calyx breaks.*—Size — small. Form short; pointed with several foliaceous apendages and several tiny hairs on surface of bud; with foliaceous parts extending beyond the tip of the bud equal to less than one-half of its length. Color — medium green, occasionally tinted with bronze (outdoors).

*As calyx breaks.*—Color — red.

*Opening.*—Opens well in all weather.

Bloom:

*Size when fully open.*—Small, averaging about 35 mm (1½").

*Petalage very double.*—Averaging 50 petals or more, arranged regularly plus sometimes several small petaloids.

*Form.*—Flat, with petals reflexing loosely outward, and later at maturity, rolled loosely outward and downward. Open flowers show no stamens.

Petals: Fairly thick; satiny on inside and on outside surface.

*Shape.*—Outside petals, broad lanceolate — with rounded tip; intermediate — broad lanceolate with rounded, sometimes acute, tip; inside — lanceolate with acute tip.

Color: Newly opened flower from a plant grown outdoors (1984 season), Dallas, Tex.

Outside petal:

*Outside surface.*—Near Currant Red 821/3 (or lighter) becoming near white at base. Note: Actual color (to the eye) appears darker than shown, in part because of blackish shadings and in part to petal sheen not picked up by color film.

Intermediate petal:

*Outside surface.*—Similar to outside petal.

*Inside surface.*—Similar to outside petal.

Inner petal:

*Outside surface.*—Same as intermediate petal.

*Inside surface.*—Same as intermediate petal. Mature flowers become lighter color as they age.

*General color effect; newly opened flowers.*—Bright medium red.

*Three days open.*—Color similar to newly opened flowers but less brilliant.

*Flower longevity.* (*October* 1984).—Plant in ground (garden) or pot 7–10 days or longer.

Reproductive organs:

*Stamens.*—Few or none.
*Pollen.*—None.
*Pistils.*—Sometimes malformed.
*Styles.*—Often malformed.
*Ovaries.*—All enclosed in calyx.
*Hips.*—None.
*Sepals.*—Permanent; spear shaped; recurved against peduncle.
*Seed.*—None.

Foliage:

*Leaves.*—Compound of five (sometimes three or seven) leaflets; small; leathery; semi-glossy.
*Leaflets.*—Shape: broad, lanceolate, apex acute; base rounded or rounded acute. Margin serrate. Color: medium green; new growth — normal (medium) green. Rachis: medium strength; upperside quite smooth; grooved; underside sparsely thorny with few or no tiny prickles. Stipules: short to medium long; narrow width; short length; narrow points which turn out usually at about 45 degrees.

Growth:

*Habit.*—Bushy; spreading; much branched.
*Growth.*—Free vigorous; internodes short.
*Canes.*—Medium; slender; weeping; prostrate.
*Main stems.*—Color: medium green.

*Thorns.*—Several; slender straight, inclined slightly downward; color; tan. Prickles — none. Hairs — none.
*Branches.*—Color: medium green. Thorns: several; short to medium length; slender; nearly straight, inclined downward. Medium oval base. Prickles: none. Hairs: none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dense, much branched, prostrate (spreading) habit, substantially as illustrated and described, characterized by buds and flowers of a medium red color, being of a shade generally near (or similar to) Currant Red 821/3, the bud and flower resembling the variety Red Cascade (U.S. Plant Pat. No. 3,962) in the form and size; and further characterized by a plant of vigorous, much branched, prostrate growth habit, easy to propagate from cuttings, with an abundance of flowers borne usually in clusters of 5 to 15.

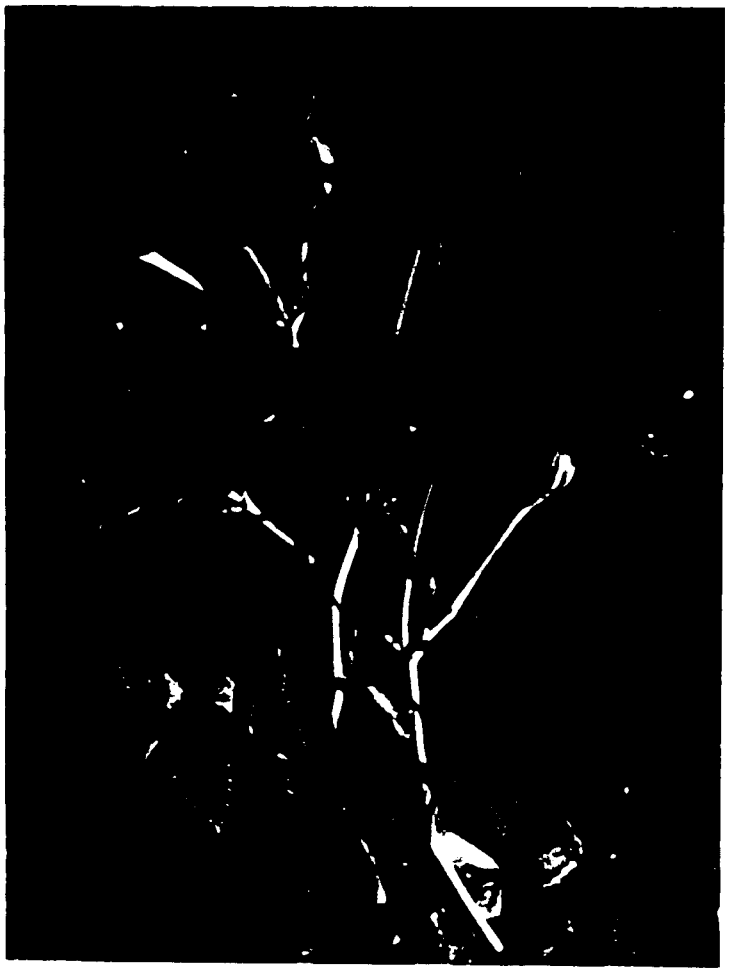
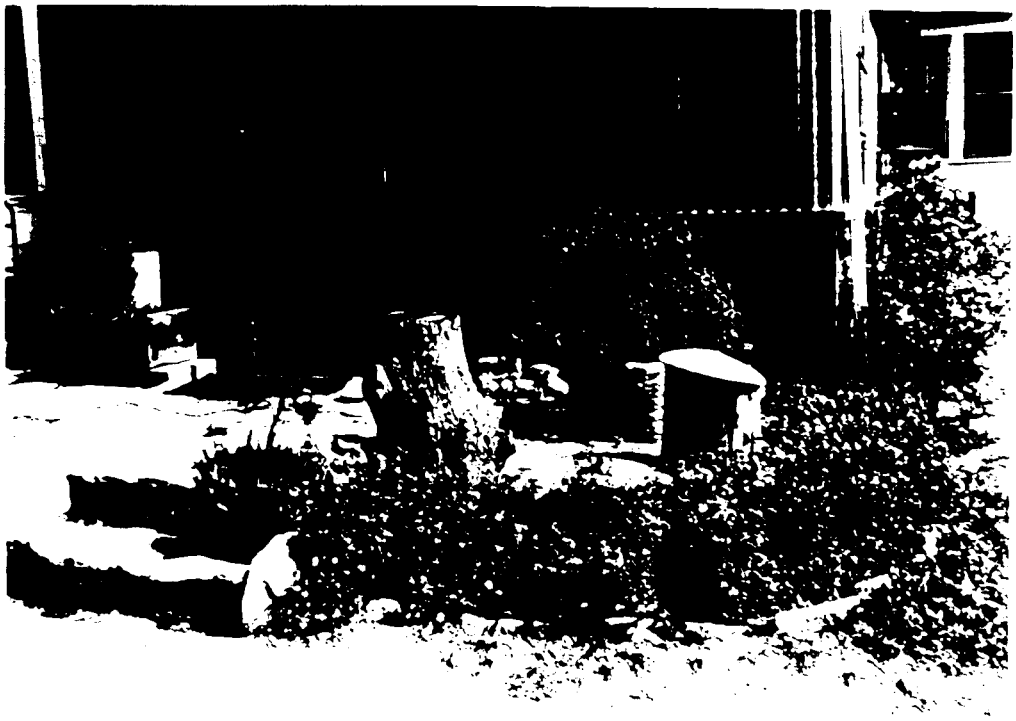

* * * * *